United States Patent
Parkins

(10) Patent No.: US 9,548,537 B2
(45) Date of Patent: *Jan. 17, 2017

(54) TRANSMITTER WITH IMPROVED SENSITIVITY AND SHIELDING

(71) Applicant: Red Tail Hawk Corporation, Philadelphia, PA (US)

(72) Inventor: John W. Parkins, Philadelphia, PA (US)

(73) Assignee: Red Tail Hawk Corporation, Philadelphia, PA (US)

( * ) Notice: Subject to any disclaimer, the term of this patent is extended or adjusted under 35 U.S.C. 154(b) by 52 days.

This patent is subject to a terminal disclaimer.

(21) Appl. No.: 14/734,272

(22) Filed: Jun. 9, 2015

(65) Prior Publication Data
US 2015/0380821 A1    Dec. 31, 2015

Related U.S. Application Data

(63) Continuation of application No. 13/796,480, filed on Mar. 12, 2013, now Pat. No. 9,083,388.
(Continued)

(51) Int. Cl.
*H04R 1/10* (2006.01)
*H01Q 7/06* (2006.01)
(Continued)

(52) U.S. Cl.
CPC ............... *H01Q 7/06* (2013.01); *A61F 11/08* (2013.01); *H01Q 1/273* (2013.01); *H04B 5/0006* (2013.01);
(Continued)

(58) Field of Classification Search
CPC .......... H01Q 7/06; H01Q 1/273; A61F 11/08; H04B 5/0006; H04B 5/0075; H04R 1/008; H04R 1/1091
(Continued)

(56) References Cited

U.S. PATENT DOCUMENTS 2,048,604 A    7/1936 Finch
2,268,665 A    1/1942 Loewe
(Continued)

FOREIGN PATENT DOCUMENTS

DE    3508830 A1    9/1986
DE    3826294 A1    2/1990
(Continued)

OTHER PUBLICATIONS

Van Wijngaarden et al. "Development of the Wireless "Communications Earplug" for application in Military Aviation" J. Audio Eng. Soc., vol. 48, No. 6, Jun. 2000.
(Continued)

*Primary Examiner* — MD Talukder
(74) *Attorney, Agent, or Firm* — Brown & Michaels, PC

(57) ABSTRACT

A magnetic field transmitter, especially a transmitter used in conjunction with wireless communications earplugs. In one embodiment, a plate of magnetic material is used behind a coil of electrical conductor to improve the efficiency of the transmitter and to provide electrical and magnetic shielding. The specific dimensions and characteristics of the preferred embodiment of the transmitter described herein provide for efficient wireless communications.

18 Claims, 4 Drawing Sheets

Related U.S. Application Data

(60) Provisional application No. 61/694,481, filed on Aug. 29, 2012.

(51) Int. Cl.

| | | |
|---|---|---|
| *H04B 5/00* | (2006.01) | |
| *A61F 11/08* | (2006.01) | |
| *H01Q 1/27* | (2006.01) | |
| *H04R 25/00* | (2006.01) | |

(52) U.S. Cl.
CPC .......... *H04B 5/0075* (2013.01); *H04R 1/1008* (2013.01); *H04R 1/1091* (2013.01); *H04R 25/554* (2013.01); *H04R 2209/022* (2013.01); *H04R 2420/07* (2013.01)

(58) Field of Classification Search
USPC ........ 455/41.1, 41.2, 41.3; 381/74, 345, 353
See application file for complete search history.

(56) References Cited

U.S. PATENT DOCUMENTS

| | | |
|---|---|---|
| 2,530,621 A | 11/1950 | Lybarger et al. |
| 3,125,646 A | 3/1964 | Lewis |
| 3,322,897 A | 5/1967 | Vozeolas et al. |
| 3,752,939 A | 8/1973 | Bartz |
| 4,150,262 A | 4/1979 | Ono |
| 4,957,478 A | 9/1990 | Maniglia |
| 4,972,491 A | 11/1990 | Wilcox, Jr. |
| 5,073,947 A | 12/1991 | Reddemann et al. |
| 5,343,532 A | 8/1994 | Shugart, III |
| 5,396,563 A | 3/1995 | Yoshimi |
| 5,420,930 A | 5/1995 | Shugart, III |
| 5,701,348 A | 12/1997 | Shennib et al. |
| 5,796,821 A | 8/1998 | Crouch et al. |
| 6,012,812 A | 1/2000 | Rickards |
| 6,078,675 A | 6/2000 | Bowen-Nielsen et al. |
| 6,208,740 B1 | 3/2001 | Grever |
| 6,438,245 B1 | 8/2002 | Taenzer et al. |
| 6,694,034 B2 | 2/2004 | Julstrom et al. |
| 6,823,171 B1 | 11/2004 | Kaario |
| 6,925,179 B2 | 8/2005 | Waldron et al. |
| 7,206,426 B1 | 4/2007 | Julstrom et al. |
| 8,116,494 B2 | 2/2012 | Rass |
| 2002/0061113 A1 | 5/2002 | van Halteren et al. |
| 2002/0141545 A1 | 10/2002 | Segovia |
| 2003/0003864 A1 | 1/2003 | Locke |
| 2003/0031339 A1 | 2/2003 | Marshall et al. |
| 2003/0219135 A1 | 11/2003 | Morimoto |
| 2004/0151334 A1 | 8/2004 | Vaudrey et al. |
| 2004/0258261 A1 | 12/2004 | Cochran et al. |
| 2005/0018859 A1 | 1/2005 | Buchholz |
| 2005/0078848 A1 | 4/2005 | Hlibowicki |
| 2005/0094830 A1 | 5/2005 | Stanley |
| 2005/0245213 A1* | 11/2005 | Hirano .................. H03F 1/0205 455/127.1 |
| 2005/0260953 A1 | 11/2005 | Lefler |
| 2006/0013420 A1 | 1/2006 | Sacha |
| 2006/0025179 A1 | 2/2006 | Kim |
| 2006/0269088 A1 | 11/2006 | Julstrom et al. |
| 2007/0041602 A1 | 2/2007 | Killion |
| 2007/0041606 A1 | 2/2007 | Sheppard, Jr. |
| 2007/0149261 A1 | 6/2007 | Huddart |
| 2007/0153444 A1 | 7/2007 | Groh et al. |
| 2008/0025524 A1 | 1/2008 | Vaudrey et al. |
| 2008/0132193 A1* | 6/2008 | Petrovic ................... H04B 1/28 455/323 |
| 2009/0041285 A1 | 2/2009 | Parkins |
| 2009/0143097 A1 | 6/2009 | Wilson |
| 2010/0016827 A1 | 1/2010 | Hunter et al. |
| 2010/0278371 A1 | 11/2010 | Hanada |
| 2010/0296667 A1 | 11/2010 | Parkins |
| 2011/0081936 A1* | 4/2011 | Haim ................ H04W 52/367 455/522 |
| 2011/0103605 A1 | 5/2011 | Killion et al. |
| 2011/0130622 A1 | 6/2011 | Ilberg |
| 2012/0021704 A1* | 1/2012 | Chan .................... H03G 3/3042 455/95 |
| 2012/0275638 A1 | 11/2012 | Chang |
| 2013/0244722 A1* | 9/2013 | Rousu ................ H04B 1/0057 455/552.1 |
| 2014/0295909 A1* | 10/2014 | Ouchi ................ H04W 52/242 455/522 |

FOREIGN PATENT DOCUMENTS

| | | |
|---|---|---|
| DE | 10117705 A1 | 10/2001 |
| WO | 2006042298 A2 | 4/2006 |

OTHER PUBLICATIONS

International Search Report and Written Opinion for PCT Application No. PCT/US2013/056819 Issued on May 30, 2014.

SJSU "Electromagnetic Induction", http://www.physics.sjsu.edu/becker/physics51/induction.htm; pp. 1-23; Jan. 2007.

* cited by examiner

TRANSMITTER WITH IMPROVED SENSITIVITY AND SHIELDING

REFERENCE TO RELATED APPLICATIONS

This is a continuation patent application of copending application Ser. No. 13/796,480, filed Mar. 12, 2013, entitled "Transmitter with Improved Sensitivity and Shielding", which claimed benefit under 35 USC §119(e) of provisional application No. 61/694,481, filed Aug. 29, 2012, entitled "Transmitter with Improved Sensitivity and Shielding". The aforementioned applications are hereby incorporated herein by reference.

ACKNOWLEDGMENT OF GOVERNMENT SUPPORT

This invention was conceived during a Navy Phase 2.5 SBIR contract N68335-09-C-0003. The government has certain rights in the invention.

BACKGROUND OF THE INVENTION

Field of the Invention

This invention concerns magnetic field transmitters, especially transmitters that are used in conjunction with wireless communications earplugs.

Description of Related Art

The inventor's co-pending U.S. patent application Ser. No. 11/837,129, entitled "Wireless Communications Headset System Employing a Loop Transmitter that Fits Around the Pinna" describes a loop transmitter comprising a coil of wire having an open center sized to fit around a pinna of a user's ear for use with communications earplugs. This invention is very effective in situations where there is limited volume available behind the human pinna such as when the transmitter is located in a shallow headset earcup or helmet, or other such applications, and the transmitter would otherwise be in contact with the pinna due to lack of space. However, larger transmitter coils are less efficient compared to smaller transmitters because they generate more unused magnetic flux. High efficiency transmitters are desirable in battery-operated devices because these devices would run longer on a single charge. Therefore, when space is available for a particular loop transmitter, it is desirable in many applications to employ a higher efficiency loop transmitter.

SUMMARY OF THE INVENTION

This invention concerns magnetic field transmitters, especially transmitters that are used in conjunction with wireless communications earplugs. In one embodiment, a plate of magnetic material is used behind a coil of electrical conductor to improve the efficiency of the transmitter and to provide electrical and magnetic shielding. The specific dimensions and characteristics of the preferred embodiment of the transmitter described herein provide for efficient wireless communications.

DETAILED DESCRIPTION OF THE INVENTION

This invention concerns magnetic field transmitters, especially transmitters that are used in conjunction with wireless communications earplugs. In one embodiment, a plate of magnetic material is used behind a coil of electrical conductor to improve the efficiency of the transmitter and to provide magnetic and electrical shielding. The coil geometry of the invention improves efficiency for wireless communications with a wireless earplug.

Figure 1A:
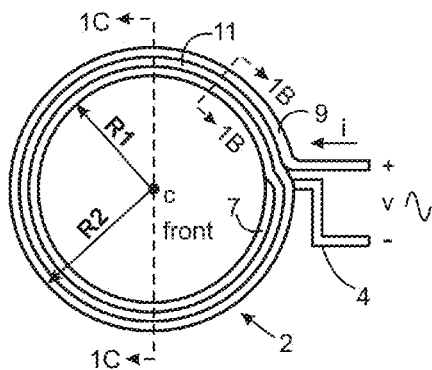
FIG. 1A shows a round coil magnetic field transmitter.
Figure 1B:
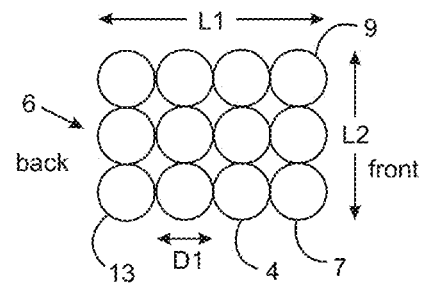
FIG. 1B shows a cross-sectional view of a portion of the embodiment shown in FIG. 1A.
Figure 1C:
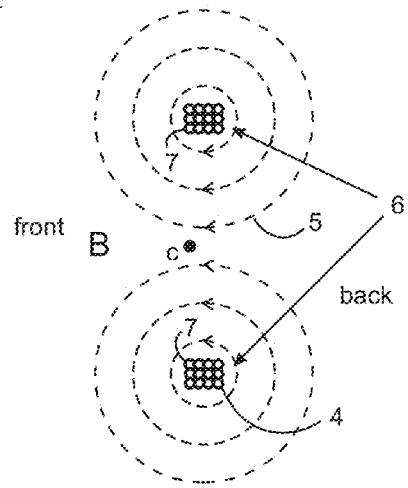
FIG. 1C shows another cross-section view of a portion of the embodiment shown in FIG. 1A and indicates magnetic field lines.

A transmitter coil 2 is shown in FIGS. 1A through 1C. The coil 2 is shown in FIG. 1A with inner radius R1 and outer radius R2 and is constructed using a continuous conductor 4 that creates loops of the coil 2. By Ohm's Law, when a voltage v is applied to the ends of the conductor 4, a current i results, and, inversely, when a current i is applied to the ends of the conductor 4, a voltage v results. The current i flows into a first loop 9, followed by a second loop 11, followed by an inner front loop 7 and continues through all loops exiting after the last loop 13 seen in FIG. 1B.

FIG. 1B is a cross section along the lines 1B-1B in FIG. 1A. The wound conductor 4 creates a conductor bundle 6 with annulus width L2 and annulus depth L1, where L2=R2−R1. In this example, the conductor bundle cross section indicates a coil 2 of three rows and four columns indicating twelve loops. The conductor 4 has diameter D1.

FIG. 1C shows the cross section along the lines 1C-1C in FIG. 1A. Two cross sections of the conductor bundle 6 can be seen. Current i flowing into conductor 4 in FIG. 1A results in magnetic field B and circulating magnetic field lines 5 (shown as dashed lines).

Magnetic field lines 5 are shown here as circular lines for illustrative purposes; however, in reality they would have a more complicated rectangular shape. Moreover, only six magnetic field lines 5 are shown whereas there are infinitely many. The magnetic field lines 5 are symmetric front to back. If the current i corresponds to a communications signal, the magnetic field can be sensed by a wireless receiver and used for wireless communications.

Between the conductor bundle 6 cross sections, the magnetic field B is generally uniform and pointing in the same direction to the front. The magnetic flux density generated by the inner front loop 7 of the coil 2 at inner front loop center point c when placed in a vacuum is given by $B=u_o i/(2 R1)$, where B is the magnetic flux density (in Teslas) and the constant $u_o$ is the permeability of free space ($4\pi \times 10^{-7}$ N/A$^2$).

The total magnetic flux density generated by all the loops of the coil 2 at the center point c when placed in a vacuum is given by $B=Nu_o i/(2 Re)$ where N is the number of loops in the coil, and Re is the effective radius of the coils taken as a whole. Re can be approximated by adding all loop radii and dividing by the number of loops when the coil dimensions L1 and L2 are small compared to R1. In this example embodiment there are twelve loops in the coil, so N=12.

The electrical impedance Z seen by a voltage source into the ends of conductor 4 is Z=R+jwL, where R is the electrical resistance, j=sqrt(−1), w is the radian frequency, and L is the electrical inductance. The break frequency of the coil is defined as $f_b=R/(2\pi L)$ in Hz. At frequencies below the break frequency resistive losses (manifested as heat) become increasingly higher and the coil becomes inefficient at generating magnetic fields.

The resistance R can be calculated using the formula R=ρl/A, where ρ is the resistivity of the conductor, l is the total length of the conductor 4, A is the cross sectional area of the conductor 4 and $A=\pi(D/2)^2$.

The inductance of a single coil in a vacuum with radius R1 is given by $L=(u_o \pi R1)/2$ in Henries (H). For a coil of N loops and effective radius Re, the inductance is given by $L=N^2 (u_o \pi Re)/2$.

The imaginary power into a coil at frequencies substantially above the break frequency $f_b$ can be approximated as $P=i^2 wL$. Hence, $P=i^2 w N^2 (u_o \pi Re)/2$. If the effective coil radius Re is doubled, the power into the coil doubles, for a given current i. However, the flux density B is reduced by a factor of ½.

Higher imaginary power P requires greater actual power from battery sources and lower battery duration. Hence, all other parameters being equal, it is desirable to minimize the size of a coil 2 when the goal is to minimize the imaginary power needed to generate a flux density within a coil 2. Break frequencies between 20 Hz and 2.0 kHz are appropriate depending on the product type and design goals. Low break frequencies can be used where weight is not a concern, whereas higher break frequencies may be appropriate for products such as headsets where weight is critical.

Figure 2A:
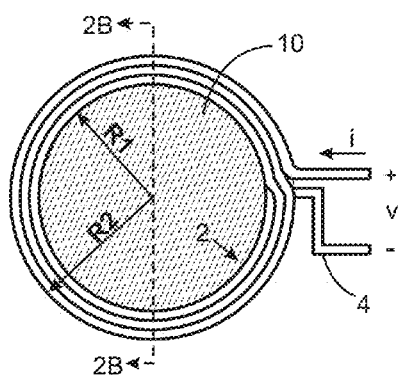
FIG. 2A shows an embodiment of the invention incorporating a magnetic backing plate.
Figure 2B:
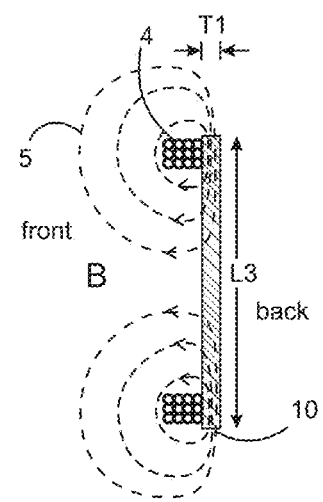
FIG. 2B shows a cross-sectional view of the embodiment shown in FIG. 2A indicating magnetic field lines.

FIG. 2A shows the coil of FIG. 1A with the addition of a magnetic backing plate 10, while FIG. 2B shows a cross section of FIG. 2A along the line 2B-2B. The magnetic backing plate 10 in FIG. 1A is attached in close proximity to the back side of the coil 2.

FIG. 2B depicts the general effect of mounting the magnetic backing plate 10. The magnetic backing plate 10 tends to draw the magnetic field lines 5 by creating a low reluctance path. Note that the magnetic field line 5 geometries shown here are approximate and are for illustrative purposes. In reality, there are an infinite number of field lines including lines that are more circular in geometry as the distance from the magnetic backing plate increases.

The effect of the magnetic backing plate 10 is to tend to project the magnetic field lines toward the front direction rather than the back direction which is desirable in circumstances such as when a wireless communications earplug is employed.

The result of adding the magnetic backing plate is to increase the inductance L of the coil, while the resistance R is unchanged. This decreases the coil 2 break frequency $f_b$ and improves the coil 2 efficiency at low frequencies.

The magnetic backing plate 10 is constructed of a material exhibiting low reluctance such as mu-metal or other low-reluctance magnetic materials. The magnetic backing plate 10 must have sufficient thickness T1 to prevent magnetic field saturation which would cause signal distortion at high field strengths. However, if the magnetic backing plate 10 is made of a conductive material, excess thickness T1 can lead to eddy current losses. This can be prevented by using a generally non-conducting material, such as magnetic ceramics, or by using laminated metal sheets with insulating material separating the layers.

In a test of the transmitter, a coil was constructed in the laboratory using 200 loops of 33 AWG conductor having a wire diameter of 0.00795 in (0.18 mm) The coil had an inner radius R1=1.40 in (35.6 mm), an outer radius R2=1.75 in (44.5 mm) and a thickness L1=0.075 in (1.9 mm) The measured inductance was 2.8 mH, while the resistance was 17 Ohms.

When a circular flat magnetic backing plate of radius 1.75 in (44.5 mm) and thickness 0.006 in (0.15 mm) and co-netic AA material was placed tightly behind the coil, the inductance increased to 3.9 mH, which is a 39% increase over the coil without the backing plate. The magnetic backing plate weighed 0.075 oz (2.13 g) while the coil weighed 0.210 oz (5.95 g). The weight of the magnetic backing plate 10 can be reduced by as much as 50%, to 0.0375 oz (1.06 g) by making perforations through the plate, without appreciably affecting the inductance, as long as the perforations are made within radius R1. This can be done because the magnetic backing plate 10 has its strongest influence in the region closest to the coil 2.

To increase the inductance by 39% by adding loops to the coil, one would have to add 18% more loops which would increase the weight by 18%. The same inductance increase using only a perforated magnetic backing plate would increase the weight by 18%.

Even though there is no weight advantage, in this example, when incorporating the magnetic backing plate 10, the magnetic backing plate 10 provides the benefit of electromagnetic shielding to protect the coil from electromagnetic radiation and to reduce radiated electromagnetic radiation.

Preferably, the magnetic backing plate 10 is electrically connected to a circuit ground point to provide improved electrical shielding. In particular, if an electronic circuit board is employed in back of the magnetic backing plate 10, the magnetic backing plate 10 shunts the magnetic field. Otherwise, the magnetic field can interfere with the electronic circuit board and eddy currents in the circuit board can partially cancel the magnetic field reduction efficiency.

Figure 3A:
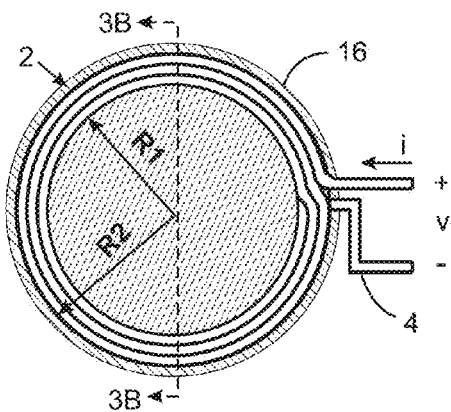
FIG. 3A shows an embodiment of the invention incorporating a cup-shaped magnetic backing plate.
Figure 3B:
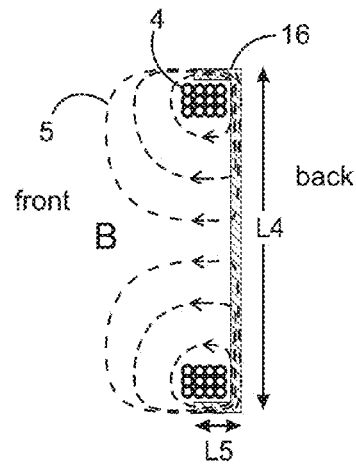
FIG. 3B shows a cross-sectional view of the embodiment shown in FIG. 3A indicating magnetic field lines.

Further improvements in the transmitter efficiency can be provided by employing a cup-shaped magnetic backing plate 16 as seen in FIGS. 3A and 3B. A cup shape can be achieved by using means such as stamping or molding. If the material is stamped, it may need to be heat treated to restore optimal magnetic properties.

An additional 16% increase in inductance can be achieved in this way compared to the disc magnetic backing plate 10 seen in FIGS. 2A and 2B. Hence, in this example, the number of loops N of the coil 2 can be reduced to achieve the same inductance with a net reduction in weight.

The inductance of the embodiment shown in FIGS. 3A and 3B increases because the cup-shaped magnetic backing plate 16 provides an improved low reluctance path for the magnetic field lines 5 around the coil 2. The magnetic field lines 5 tend to be drawn into the low reluctance cup-shaped magnetic backing plate 16. Note that the magnetic field line 5 geometries shown here are approximate and are for illustrative purposes. In reality, there are an infinite number of field lines including lines that are more circular in geometry as the distance from the cup-shaped magnetic backing plate 16 increases.

The cup-shaped magnetic backing plate 16 does not wrap completely around the coil 2 because this would shunt the magnetic field lines 5 completely around the coil 2 instead of toward the desired front direction.

Figure 4A:
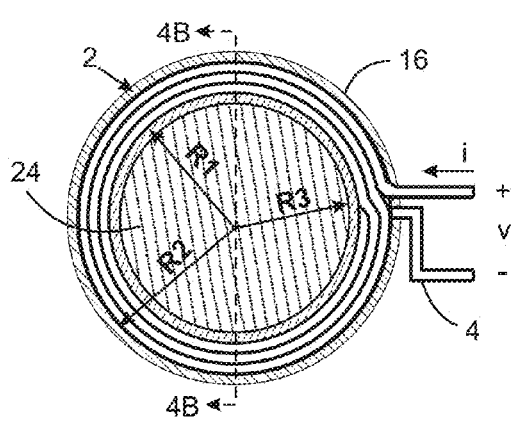
FIG. 4A shows an embodiment of the invention incorporating a cup-shaped magnetic backing plate with magnetic core.
Figure 4B:
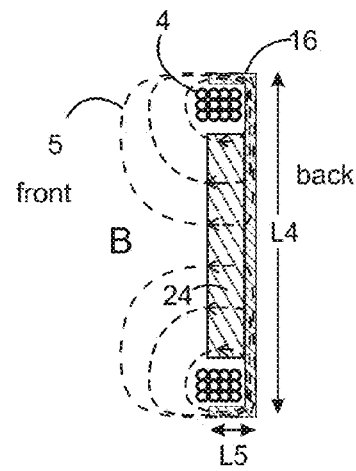
FIG. 4B shows a cross-sectional view of the embodiment shown in FIG. 4A indicating magnetic field lines.

FIGS. 4A and 4B show the embodiment of FIGS. 3A and 3B with the addition of magnetic core material 24. The core material 24 tends to shunt the magnetic field lines 5 in front of and away from the coil 2, which is desirable. However, employing core material 24 doesn't provide as much benefit because the magnetic field lines 5 are already pointed in the forward direction. The core material is preferably made of non-conductive material, such as magnetic ceramic, because there is the potential of significant eddy current losses if conductive metal was used (such eddy currents could also be reduced by forming the core with radially oriented slots).

Figure 5:
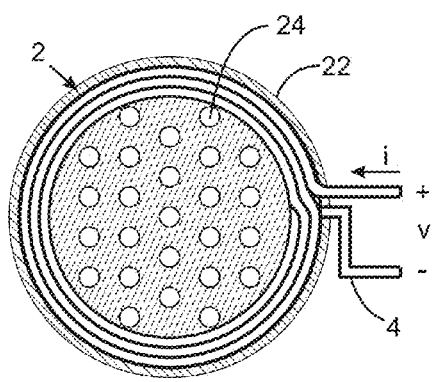
FIG. 5 shows an embodiment of the invention incorporating a perforated cup-shaped magnetic backing plate.

FIG. 5 shows an embodiment of the invention very similar to FIGS. 3A and 3B; however, this embodiment employs multiple perforations 24 to create a cup-shaped magnetic perforated backing plate 22. The perforations 24 help prevent sound from reflecting off the transmitter toward an ear or causing a reflecting surface that can yield resonances if the transmitter is used in a headset. The perforations reduce weight without reducing the inductance significantly. A single perforation, creating an annulus shape, can be used as well. However the magnetic and electrical shielding provided is diminished when using an annulus geometry.

Figure 6A:
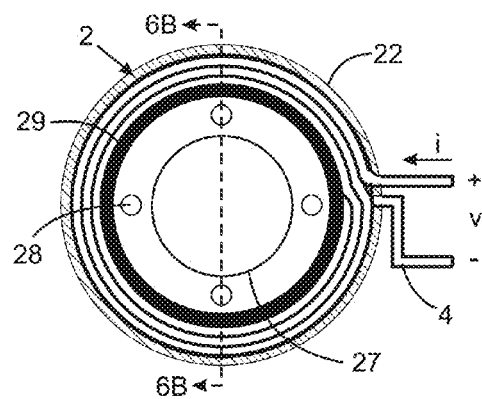
FIG. 6A shows an embodiment of the invention incorporating a perforated cup-shaped magnetic backing plate with speaker.
Figure 6B:
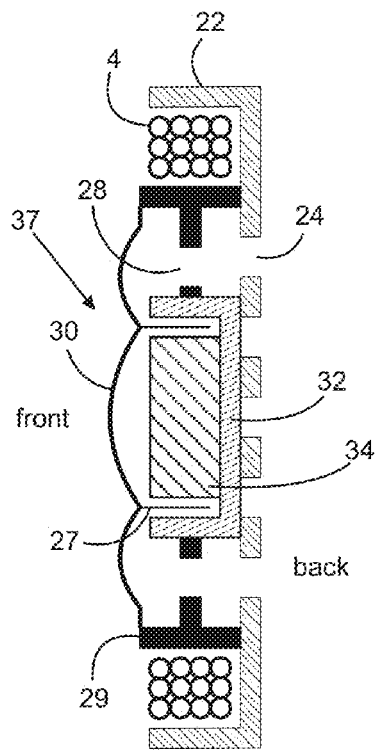
FIG. 6B shows a cross-sectional view of the embodiment shown in FIG. 6A.

The perforated backing plate 22 from FIG. 5 is employed in the embodiment shown in FIGS. 6A and 6B. The embodiment shown in FIGS. 6A and 6B is similar to the embodiment shown in FIG. 5 except that the embodiment shown in FIGS. 6A and 6B employs a speaker 37.

The speaker 37 could be a dynamic speaker, as shown in this embodiment, or could employ other types of construction such as piezoelectric, balanced armature or other type that produces sound. For clarity purposes, the electrical terminals of the speaker are not shown. An input electrical source is coupled to the electrical terminals of speakers to excite the speaker and create sound.

The speaker in this embodiment employs a housing 29 and a diaphragm 30 that moves in response to current flowing through a voice coil 27 caused by an input electrical source. The static magnetic field generated by a speaker magnet 34 and shunted by a speaker backing plate 32 creates a force on the voice coil 27 due to current flow. To reduce back pressure due to the diaphragm 30 movement, the speaker 37 employs vents 28. Four vents 28 are indicated in FIG. 6A of this embodiment.

The perforations 24 of the perforated backing plate 22 allow back pressure generated by the speaker 37 to vent. This venting provides the advantage of reducing restraining forces on the speaker diaphragm 30 resulting in improved speaker efficiency compared to incorporating a backing plate that is not perforated.

Figure 7:
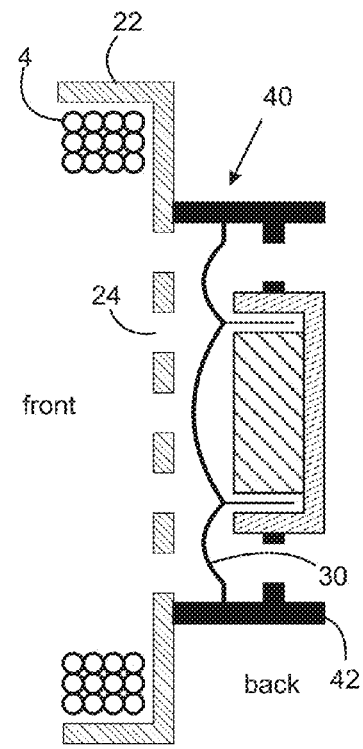
FIG. 7 shows an embodiment of the invention incorporating a perforated cup-shaped magnetic backing plate with speaker mounted to the back of the backing plate.

The embodiment shown in FIG. 7 is similar to the embodiment shown in FIGS. 6A and 6B except that a speaker 40 is employed in back of the backing plate 22 and a speaker 40 housing 42 is employed that provides a separation space for the speaker diaphragm 30 to vibrate without contacting the perforated backing plate 22. In this embodiment, the perforations 24 allow sound generated by the speaker 40 to pass through the perforated backing plate 22 to provide sound in the front direction.

Figure 8A:
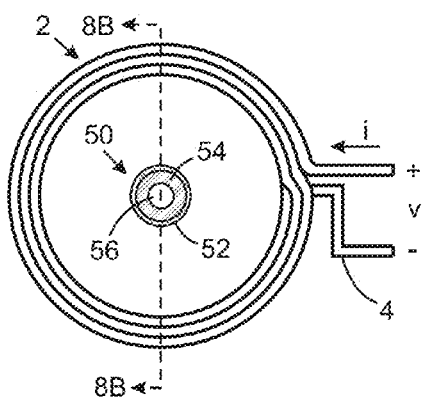
FIG. 8A shows an embodiment of the invention incorporating a wireless communications earplug.
Figure 8B:
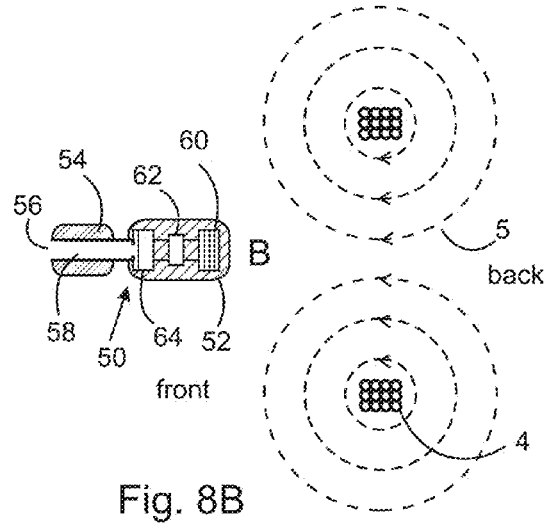
FIG. 8B shows a cross-sectional view of the embodiment shown in FIG. 8A.

FIGS. 8A and 8B are similar to the embodiment shown in FIG. 1A through 1C except that a wireless communications earplug 50 is employed. The wireless communications earplug 50 comprises a receiver coil 60 to sense the magnetic field B generated by the transmitter coil 2. The receiver coil 60 is electrically coupled to an electronics circuit 62 for processing the sensed magnetic field to provide an appropriate signal for coupling to an earplug speaker 64. The receiver coil 60, electronic circuit 62 and earplug speaker 64 are contained in an earplug housing 52. The speaker 64 is acoustically coupled to a sound delivery tube 58 for coupling to a human ear canal (not shown). An ear tip 54 made of material such as foam, rubber, plastic or other materials is used to create an acoustic seal with an ear canal. The acoustic seal prevents acoustic noise from entering the human ear canal and provides a higher acoustic impedance for the earplug speaker 64 to improve the earplug speaker 64 sensitivity.

Figure 9:
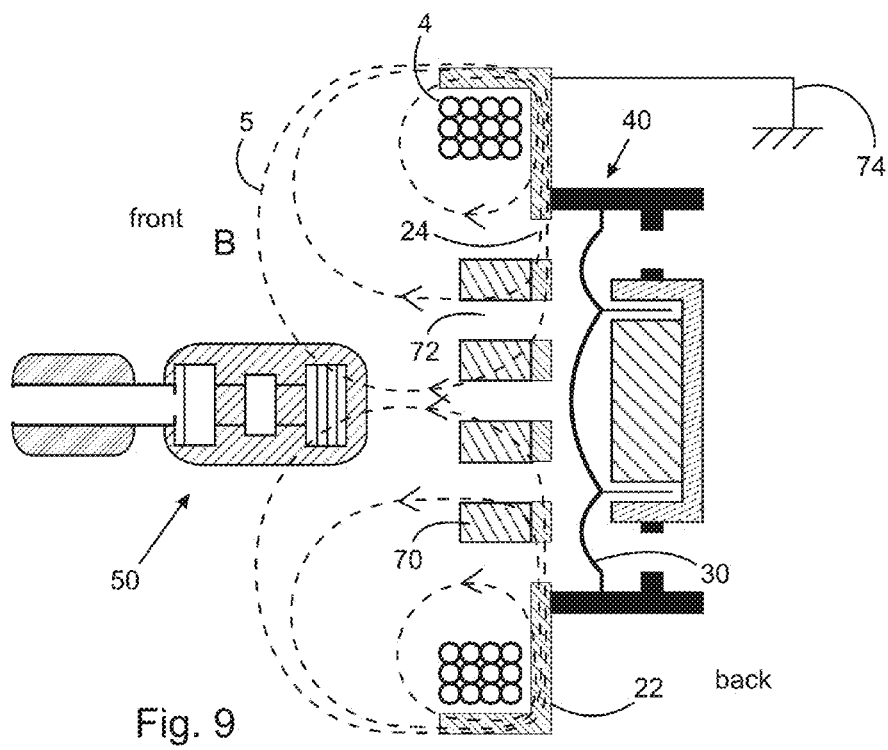
FIG. 9 shows an embodiment of the invention incorporating a wireless communications earplug, speaker and core material and indicates magnetic field lines.

FIG. 9 shows an embodiment that incorporates the wireless earplug 50 shown in FIGS. 8A and 8B with the embodiment shown in FIG. 7 and a perforated core 70. The core is perforated in this embodiment to allow sound transmission toward the front direction.

In this embodiment, a user can choose between receiving communications from the transmitter speaker 40 without using a wireless communications earplug 50, or receiving communications from the transmitter though the magnetic field B exciting the wireless communications earplug 50.

If the invention is used in a noise defending communications headset, double hearing protection can be achieved: one layer of protection being provided by headset ear cups (not shown) and the other layer being provided by the noise attenuating properties of the wireless communications earplug 50. The transmitter speaker 40 can be activated if the user loses a wireless communications earplug 50, providing backup communications. Alternatively, the transmitter speaker 40 can be active at all times.

Grounding the backing plate 22 using a grounding conductor 74 can protect a wireless communications earplug 50 from electromagnetic interference, because the earplug 50 is generally used in close proximity to the perforated backing plate 22. The shielding also protects the coil 2 from stray electromagnetic pickup. In addition, if electronics are employed within a headset ear cup, the perforated backing plate 22 provides both magnetic and electrical shielding for the electronics. Additional shielding may be used in a headset or helmet by lining the earcups and/or helmet with electrically conductive material and/or magnetic material.

The magnetic field in front of the transmitters shown in FIGS. 1 through 9 and within the inner radius R1 of the coils is fairly uniform especially within the first centimeter of the transmitters. Hence, when a wireless earplug 50 is used with the transmitters, the sensitivity of the wireless earplug 50 and sound pressure produced in a human ear canal will not vary appreciably so long as the wireless earplug 50 is within the inner radius R1 of the coil 2. Employing a larger coil 2 creates a larger region of uniform magnetic field; however, greater imaginary power is required, as described earlier. An appropriated range for the inner radius R1 of the coil is between 0.5 in (12.7 mm) and 1.25 in (32 mm) when the transmitter is used with a wireless earplug and headset. This yields coil circumscribed areas ($\pi R1^2$) of between 0.79 in$^2$ (509 mm$^2$) and 4.9 in$^2$ (3167 mm$^2$) The inventor has found from measurements in the laboratory that this range of inner radius R1 provides reasonable uniformity of magnetic field. An inner radius R1 closer to 0.5 in (12.7 mm) may be used for tighter fitting earmuffs and helmets, whereas an inner radius R1 closer to 1.25 in (32 mm) may be more appropriate for looser fitting earmuffs and helmets.

Geometries other than circular geometries may be employed for the coil, such as rectangular, oval or others. The coil circumscribed areas of these geometries should be between 0.79 in$^2$ (509 mm$^2$) and 4.9 in$^2$ (3167 mm$^2$) for reasonable efficiencies and coverage when incorporating a wireless earplug in a headset. Moreover, non-planar geometries may be employed.

Transmitter coils may be wound on bobbins to facilitate the winding process. Bobbins are commonly made of plastic or other rigid material. Magnetic backing plates may be mounted to such bobbins if desired.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A magnetic field transmitter generating a time varying magnetic field in response to a time varying input signal, comprising:
   a) a transmitter coil winding constructed of continuous conductor loops, having an inner perimeter and an outer perimeter separated by a distance, the transmitter coil winding having a coil winding resistance R and a coil winding inductance L, the inner perimeter of the loops of the transmitter coil winding, the coil winding resistance and the coil winding inductance being selected such that:
      i) the inner perimeter circumscribes an effective coil area in a range between 0.79 in$^2$ and 4.9 in$^2$;
      ii) the coil winding resistance and the coil winding inductance produces a break frequency $f_b$ for the transmitter coil winding of between 20 Hz and 2000 Hz, where the break frequency is defined by the formula $f_b=R/(2\pi L)$ wherein the coil winding resistance R is defined by the formula $R=\rho l/A$ and the coil winding inductance L is defined by the formula $L=N^2 (u_o \pi Re)/2$; and
      iii) the loops of the transmitter coil winding having an annulus width and an annulus depth which are each smaller compared to a distance from a center of the loops of the transmitter coil winding to the inner perimeter of the loops of the transmitter coil winding; and
   b) a backing plate of low reluctance magnetic material having an upper surface and a lower surface, the lower surface of the backing plate being attached in close proximity to a lower surface of the transmitter coil winding, the backing plate having an outer perimeter that is approximately coincident with the outer perimeter of the transmitter coil winding.

2. The magnetic field transmitter of claim 1, in which the backing plate is perforated with at least one perforation.

3. The magnetic field transmitter of claim 1, in which the backing plate is cup-shaped, comprising a rim with an inner surface and an outer surface, the inner surface formed in close proximity to the outer perimeter of the transmitter coil winding, extending from the upper surface of the backing plate to the upper surface of the transmitter coil winding.

4. The magnetic field transmitter of claim 1, in which the transmitter coil winding has a front surface and a back surface separated by an annular depth L1, further comprising a magnetic core substantially filling a volume defined by the inner perimeter of the transmitter coil winding and the annular depth L1.

5. The magnetic field transmitter of claim 4, where the magnetic core is perforated with at least one perforation.

6. The magnetic field transmitter of claim 4, in which the magnetic core is grounded.

7. The magnetic field transmitter of claim 1, further comprising an audio acoustic speaker integrated with the magnetic field transmitter to produce an acoustic output from the input signal.

8. The magnetic field transmitter of claim 1, further comprising a wireless ear plug communications device magnetically coupled with the magnetic field transmitter to produce an acoustic output from the input signal at the earplug.

9. The magnetic field transmitter of claim 1, in which the loops of the transmitter coil winding are circular.

10. A magnetic field transmitter generating a time varying magnetic field in response to a time varying input signal, comprising:
    a) a transmitter coil winding constructed of a bundle of continuous conductor loops, having an inner perimeter and an outer perimeter separated by a distance, an annulus width and an annulus depth, the annulus width and the annulus depth being smaller compared to a distance from a center of the loops of the transmitter coil winding to the inner perimeter of the loops of the transmitter coil winding the coil winding having a coil winding resistance and a coil winding inductance which produces a break frequency $f_b$ for the transmitter coil winding of between 20 Hz and 2000 Hz, where the break frequency is defined by the formula $f_b=R/(2\pi L)$, wherein the coil winding resistance R is defined by the formula $R=\rho l/A$ and the coil winding inductance L is defined by the formula $L=N^2 (u_o \pi Re)/2$;
    b) a backing plate of low reluctance magnetic material having a front side and a back side, the transmitter coil winding being fixedly attached in close proximity to the front side of the backing plate, the backing plate having an outer perimeter that is approximately coincident with the outer perimeter of the transmitter coil winding and a central area perforated with at least one perforation passing through the upper surface and the lower surface; and
    c) an audio acoustic speaker for producing an acoustic output from the input signal, mounted adjacent to the at least one perforation in the backing plate, such that sound generated by the speaker passes through the at least one perforation in the backing plate.

11. The magnetic field transmitter of claim 10, in which the inner perimeter of the transmitter coil winding circumscribes an effective coil area in a range between 0.79 in$^2$ and 4.9 in$^2$.

12. The magnetic field transmitter of claim 10, in which the transmitter coil winding has a coil winding resistance R and a coil winding inductance L, the coil winding resistance and the coil winding inductance being selected to produce a break $f_b$ for the transmitter coil winding of between 20 Hz and 2000 Hz, where the break frequency is defined by the formula $f_b=R/(2\pi L)$.

13. The magnetic field transmitter of claim 10, where the magnetic backing plate is cup-shaped, comprising a rim with an inner surface and an outer surface, the inner surface formed in close proximity to the outer perimeter of the coil winding, extending from the front side of the backing plate to the upper surface of the transmitter coil winding.

14. The magnetic field transmitter of claim 10, in which the transmitter coil winding has a front surface and a back surface separated by an annular depth L1, further comprising a magnetic core substantially filling a volume defined by the inner perimeter of the coil winding and the annular depth L1, the magnetic core being perforated by at least one perforation aligned with the at least one perforation of the backing plate.

15. The magnetic field transmitter of claim 14, in which the magnetic core is grounded.

16. The magnetic field transmitter of claim 10, further comprising a wireless ear plug communications device magnetically coupled with the magnetic field transmitter to produce an acoustic output from the input signal at the earplug.

17. The magnetic field transmitter of claim 10, in which the loops of the transmitter coil winding are circular.

18. The magnetic field transmitter of claim 10, in which the speaker is in a speaker housing mounted to the back side of the backing plate, the housing providing a separation space for a speaker diaphragm to vibrate without contacting the backing plate.

\* \* \* \* \*